United States Patent
Scherlen et al.

(10) Patent No.: US 11,921,362 B2
(45) Date of Patent: Mar. 5, 2024

(54) METHOD FOR DETERMINING A FILTER FOR A TRANSPARENT SUPPORT BASED ON A DETERMINED INDIVIDUAL LIGHT SENSITIVITY

(71) Applicant: ESSILOR INTERNATIONAL, Charenton-le-Pont (FR)

(72) Inventors: Anne-Catherine Scherlen, Charenton-le-Pont (FR); Camille Ehrismann, Charenton-le-Pont (FR); Sarah Marie, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 17/621,280

(22) PCT Filed: Jun. 17, 2020

(86) PCT No.: PCT/EP2020/066776
§ 371 (c)(1),
(2) Date: Dec. 21, 2021

(87) PCT Pub. No.: WO2020/254415
PCT Pub. Date: Dec. 24, 2020

(65) Prior Publication Data
US 2022/0350171 A1    Nov. 3, 2022

(30) Foreign Application Priority Data
Jun. 21, 2019  (EP) .................................... 19305810

(51) Int. Cl.
*G02C 7/10* (2006.01)
*A61B 3/06* (2006.01)

(52) U.S. Cl.
CPC ................ *G02C 7/10* (2013.01); *A61B 3/063* (2013.01)

(58) Field of Classification Search
CPC .................................. G02C 7/10; A61B 3/063
(Continued)

(56) References Cited

U.S. PATENT DOCUMENTS

| 2008/0221674 A1* | 9/2008 | Blum ....................... G02C 7/04 623/5.11 |
| 2012/0120515 A1* | 5/2012 | Ishak ..................... G02C 7/049 359/885 |

(Continued)

FOREIGN PATENT DOCUMENTS

| AU | 2017263133 | 12/2018 |
| CN | 105164576 | 12/2015 |

(Continued)

OTHER PUBLICATIONS

Extended European Search Report & Opinion issued in priority application EP 193058104, dated Jan. 27, 2020.
(Continued)

*Primary Examiner* — William R Alexander
*Assistant Examiner* — Sharrief I Broome
(74) *Attorney, Agent, or Firm* — Norton Rose Fulbright US LLP (57) ABSTRACT

The invention provides a method for determining at least one filter for a transparent support, the method comprising the following steps: —determining a quantity representative of a light sensitivity threshold of the user; —determining, for each light environment among a group of light environments, an index representative of the level of protection required by the user; —determining a score for each light environment among the group of light environments (40) and for each filter among a group of filters, said score being representative of the capacity of the filter to reach the level of protection required by the user, determining at least one filter among the group of filters based on the scores of said (Continued)

at least one filter in a plurality of light environments (40) among the group of light environments.

13 Claims, 7 Drawing Sheets

(58) Field of Classification Search
USPC .................. 351/159.6, 159.7, 159.39, 159.73
See application file for complete search history.

(56) References Cited

U.S. PATENT DOCUMENTS

| 2014/0268025 | A1* | 9/2014 | Legerton | .................. | G02C 7/10 |
| | | | | | 351/159.61 |
| 2017/0038605 | A1 | 2/2017 | Legerton | | |
| 2017/0371179 | A1* | 12/2017 | Scherlen | .................. | G02C 7/10 |
| 2019/0212581 | A1* | 7/2019 | Scherlen | ................. | G02C 7/101 |

FOREIGN PATENT DOCUMENTS

| CN | 107111162 | 8/2017 |
| CN | 107111165 | 8/2017 |

OTHER PUBLICATIONS

International Search Report & Opinion issued in priority application PCT/EP2020/066776, dated Sep. 28, 2020.
Office Action issued in corresponding Chinese Application No. 202080044582.7, dated Dec. 11, 2023 (English Machine Translation).

* cited by examiner

|  | Intensity | Spatial | Spectral | Temporal |
|---|---|---|---|---|
| Intense lights with reflections | *** | | | |
| Outdoor fun sun | ** | | | |
| Outside-cloudy day very luminous | * | | * | |
| Supermarket | | ** | ** | * |
| Office with many lights and computers | * | * | ** | |
| Inside the house | * | * | * | |
| Night situation with digital device | ** | ** | * | |
| Night driving | ** | ** | ** | ** |

METHOD FOR DETERMINING A FILTER FOR A TRANSPARENT SUPPORT BASED ON A DETERMINED INDIVIDUAL LIGHT SENSITIVITY

CROSS-REFERENCE TO RELATED APPLICATIONS

This application is a national phase application under 35 U.S.C. § 371 of International Application No. PCT/EP2020/066776 filed 17 Jun. 2020, which claims priority to European Patent Application No. 19305810.4 filed 21 Jun. 2019. The entire contents of each of the above—referenced disclosures is specifically incorporated by reference herein without disclaimer.

The present invention generally relates to the field of light sensitivity.

It more particularly relates to a method for determining at least one filter intended to be placed in front of the eye of a user, said filter being able to improve or to maintain the visual comfort and/or visual performance of said user.

It also relates to a computer system and a computer program product comprising code instructions for performing said method.

It has been observed that most people, close to 9/10 people, experience sensitivity to light. It can be a sensation of headache, pain, dazzling, or fatigue. It is a visual discomfort which can occur in many lighting conditions, notably in lighting conditions specific for a given user.

Both users & eye care professionals (ECP) are conscious of the light sensitivity issue but it is difficult to engage conversation on that specific issue and find a solution to address it in most cases. Indeed, it appears that known methods are unsatisfactory to determine a filter which really fits the individual light sensitivity of the user.

These known methods for determining filters are generally based on procedures that are either:
- subjective and are thus too dependent on the user's judgment, or
- objective but limited to the measurements performed on the user whereas light sensitivity issue comprises an important component perception based on the user's perception.

In both cases, the subjective and objective methods do not allow to determine all the factors of the light sensitivity issue so that the determined filter does not fully fit the individual needs of the user.

A problem that the invention aims to solve is thus to provide a method allowing to determine a filter for a transparent support which can better fulfill the level of protection needed by the user, taking into account the user's perception of its visual discomfort.

To solve this problem, the invention provides a method for determining at least one filter for a transparent support able to improve or to maintain the visual comfort and/or visual performance of a user, the method comprising the following steps:
- determining a quantity representative of a light sensitivity threshold of the user;
- determining, for each light environment among a group of light environments, an index representative of the level of protection required by the user;
- determining a score for each light environment among the group of light environments and for each filter among a group of filters, said score being representative of the capacity of the filter to reach the level of protection required by the user;
- determining at least one filter among the group of filters based on the scores of said at least one filter in a plurality of light environments among the group of light environments.

This method proposes to determine a filter by both considering a quantity representative of a light sensitivity threshold, i.e. an objective parameter or a parameter obtained using a measurement/calculation process, and a level of protection required by the user himself, i.e. a subjective parameter. The filter is thus determined from an array of parameters considering both the physical response of the user to light stimuli and the user's perception to predetermined uncomfortable light environments to better determine the user's needs. Hence, a filter with a better compliance to the level of protection needs for given light environments and which is specific to his individual needs can be provided to the user.

According to an embodiment of the determining method, the group of light environments is selected among a set of environments; each environment of the set of environments being associated with a given light level.

According to an embodiment of the determining method, the environments of the set of environments are associated with light levels different from each other.

According to an embodiment of the determining method, the group of light environments is selected among the set of light environments based on a questionnaire assessing the recurrence of each light environment for the user and/or the level of discomfort of each light environment for the user.

According to an embodiment of the determining method, the index representative of the level of protection required by the user in a given light environment among the group of light environments is calculated based on the light level associated with said light environment and on the determined light sensitivity threshold.

According to an embodiment of the determining method, the score for a given filter and a given light environment is calculated based on the index representative of the level of protection required by the user in said light environment and an index representative of the protection provided by said filter.

According to an embodiment of the determining method, the index representative of the protection provided by a given filter is determined based on the luminous transmittance of the given filter.

According to an embodiment of the determining method, the light sensitivity threshold is determined using a device configured to expose the user to an increasing light level and to determine the user's light sensitivity threshold based on a user's feedback representative of a discomfort.

According to an embodiment of the determining method, the light sensitivity threshold is determined when the user is exposed to at least one light condition among a warm light, a cold light and a blinking light.

According to an embodiment of the determining method, the step of determining at least one filter comprises the following steps:
- associating each score with a value representative of the compliance of a given filter in a given light environment in view of the level of protection required by the user;
- for a plurality of filters among the group of filters, calculating the sum of the values of the plurality of light environments; and
- ranking the plurality of filters using the sum obtained at preceding step.

According to an embodiment of the determining method, said method further comprises at least one among the following steps:
- displaying on a displaying device the light sensitivity threshold using a predetermined scale based on a population baseline,
- displaying on the displaying device a discomfort level representative of the level of discomfort declared by the user for each light environment among the group of light environments,
- displaying on the displaying device the at least one filter determined among the group of filters.

According to an embodiment of the determining method, the method is a computer-implemented method.

The invention also provides a computer system for determining at least one filter for a transparent support able to improve or to maintain the visual comfort and/or visual performance of a user, the system comprising:
- a processor; and
- a memory with computer code instructions stored thereon, the memory operatively coupled to the processor such that, when executed by the processor, the computer code instructions cause the computer system to perform a method for determining at least one filter for a transparent support able to improve or to maintain the visual comfort and/or visual performance of a user, the method comprising the following steps:
  - determining a quantity representative of a light sensitivity threshold of the user;
  - determining, for each light environment among a group of light environments, an index representative of the level of protection required by the user;
  - determining a score for each light environment among the group of light environments and for each filter among a group of filters, said score being representative of the capacity of the filter to reach the level of protection required by the user;
  - determining at least one filter among the group of filters based on the scores of said at least one filter in a plurality of light environments among the group of light environments.

The invention further provides a computer program product comprising code instructions for performing a method for determining at least one filter for a transparent support able to improve or to maintain the visual comfort and/or visual performance of a user, the method comprising the following steps:
- determining a quantity representative of a light sensitivity threshold of the user;
- determining, for each light environment among a group of light environments, an index representative of the level of protection required by the user;
- determining a score for each light environment among the group of light environments and for each filter among a group of filters, said score being representative of the capacity of the filter to reach the level of protection required by the user;
- determining at least one filter among the group of filters based on the scores of said at least one filter in a plurality of light environments among the group of light environments.

The invention is described in more detail below by way of the figures that show only one preferred embodiment of the invention.

The present invention provides a method for determining at least one filter for a transparent support. According to a preferred embodiment, the filter determining method is a computer-implemented method. The present invention further provides a computer system and a computer program product comprising code instructions for performing said method.

The filter determining method allows to determine at least one filter which fulfills the level of protection required by a user based on an improved determination of the user's sensitivity of light. The light sensitivity refers to any relatively intense and prolonged reaction or modification of comfort or visual performance in relation to a temporary or continuous light flux or stimuli.

By "transparent support", we mean any support through which light may pass and onto which a filter can be disposed to modulate light transmission. The transparent support may be any support intended to be disposed on or in front of an eye of the user. Furthermore, the transparent support may be an ophthalmic lens, a lighting device, an illuminated display, a windshield, a head-mounted display (called "HMD"), a glass, a glass of a portable terminal, etc.

By "filter", we mean any means able to modulate light, particularly at least one component of the light (see "4D" below). The filter may be a filter coating or a filtering function which can be used to provide a filter coating. The filter may be in the form of a passive filter (uniform, with a gradient or with a spatial variation) or an active filter as photochromic or electrochromic filters.

It has been observed that a light environment cannot be accurately defined by only considering a single parameter as light intensity, this light environment is dynamic and composed of a plurality of components allowing to better describe thereof. Light may be defined as comprising four main components (called "4D"): an intensity component, a spatial component, a temporal component and a spectral component.

The intensity component refers to the luminous flux emitted by a light source in LUmen. The intensity component induces an illuminance at the wearer's position expressed in Lux. The illuminance may be determined using a light sensor disposed at a user's eye position which measures the illuminance in Lux induced by a light source. Some of the factors affecting the illuminance are the energetic intensity of a light source (the initial volume), the distance between the user and the source (the volume at any point along a light path) and any modifying elements in the light path (air, clouds, filters, reflectors, etc.). For example, the amount of outdoor light a person is exposed to can vary depending on geographical location, season, time of day, local weather, etc.

The spatial component is the relative position of the light source regarding the user. This relative position depends on the angular distance between the user and the light source. The spatial component can be punctual or wide, and it can affect the individual's perception of light. Thus, for a given radiant flux, a punctual light source will have a higher luminance due to its smaller size. For example, vehicle headlights of similar radiant flux differ in luminance according to their size and distance.

The temporal component defines the period during which the light source emits. Indeed, light may be present for a short or long period of time, which may change the perception of the light by the user. Exposure to light for a given duration may be continuous or intermittent (which may also vary in frequency). For instance, car headlamps may only contribute to the light environment for a few seconds and move constantly across the field of vision.

The spectral component refers to the spectrum of the light which is emitted and its associated energy. This spectrum may be expressed using the wavelength of the light flux in nanometers. As an example, the visible spectrum of the light is comprised between 380 nm and 780 nm. A light flux of white light may appear warmer or colder depending on its spectrum.

The level of protection needed by a user can be better defined when considering a determining method which takes into account all these light components to define light environments. The contribution of this definition of the light in the filter determining method is detailed later in this description.

Figure 1:
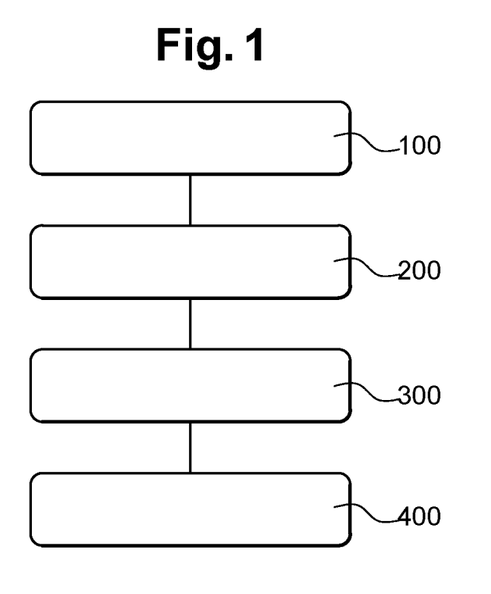
FIG. 1 schematically shows a flowchart of a filter determining method.

As shown on FIG. 1, the filter determining method comprises a step 100 of determining a quantity representative of a light sensitivity threshold of the user, a step 200 of determining an index representative of the level of protection required by the user for specific light environments, a step 300 of determining a score for each light environment and for a plurality of filters and a step 400 of determining at least one filter based on the scores determined at step 300.

The light sensitivity determining step 100 comprises the determination of a quantity representative of a light sensitivity threshold of the user. This quantity is preferably an illuminance expressed in lux.

Figure 2:
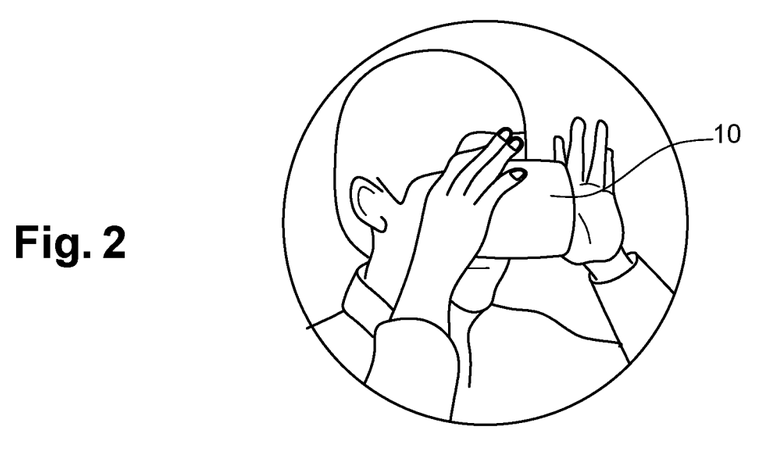
FIG. 2 schematically shows a light sensitivity test performed using a dedicated device.

The light sensitivity threshold may be determined based on measurements using a dedicated device. This dedicated device may be device 10 configured to emit light toward one or both eyes of the user, as shown on FIG. 1. The device 10 is configured to expose the user to an increasing/decreasing light level and to determine the user's light sensitivity threshold based on a user's feedback representative of a discomfort. The light intensity is increased or decreased to form a light varying sequence. Preferably, this sequence comprises increasing light intensity so as to start light emission with a comfortable intensity for the user. The light sensitivity threshold is then determined depending on a response provided by the user. This response may be intentional by asking the user to indicate when a discomfort really disturbing occurs or determined by an external device configured to detect physical response to the user to a given light flux. In both cases, the quantity representative of a light sensitivity threshold of the user may be determined as the illuminance for which a response of the user is detected.

Furthermore, the light sensitivity threshold may be determined for different colors of light to obtain a threshold reflecting cold or warm white light. Emitting light reflecting a cold or warm light, e.g. by emitting more blue light or more red light, allows to respectively simulate substantially artificial or natural light or different light ambiance. Varying the color of light emitted toward the user allows to vary the light spectrum. Light sensitivity of the user can thus be determined with regard to a variation of the spectral component of the light.

This light sensitivity determining step 100 is for example performed as follows. The device 10 is disposed in front of the eyes of the user and a light source emits a light flux toward the eyes of the user. A measurement sequence is performed comprising three measurement steps. The first measurement step is a continuous light emission to induce an illuminance from a minimum to a maximum values increasing the illuminance by stages, e.g. from 25 Lux to 10211 Lux. For example, the light emission may start with an illuminance of 25 Lux for 5 seconds to adapt the eye to the light condition and cancel all previous light exposure before the measurement and then continue with an increase of the illuminance of 20% each second to the maximum illuminance. In a more general way, the light may be emitted to induce an illuminance varying from 25 Lux to 15000 Lux. This first measurement step is performed with warm light.

The second measurement step is performed identically to the first measurement step but with cold light.

Then, the third measurement step is a flashing light emission to induce an illuminance from a minimum value to a maximum value increasing the illuminance by stages, e.g. from 25 Lux to 8509 Lux. The illuminance of the flashing light emission is preferably increased by at least 30%, preferably by 40%, most preferably by at least 44%. Before and between each flash light emission, the user is subjected to a light emission lower than the minimum value of illuminance of the flashing light emission, e.g. 10 Lux. The time of each flashing light emission is preferably 0.5 s and the time between each flashing light emission is preferably 2 s.

According to a preferred embodiment, at least one of the first, second and third measurement steps is performed to determine the light sensitivity threshold of the user. A quantity representative of the light sensitivity threshold of the user is thus determined on the basis of the results obtained with at least one of said first, second and third measurement steps. Regarding the definition of light described above, this light sensitivity determining step 100 allows to determine a quantity representative of the light sensitivity threshold with regard to a variation of the intensity, the spatial, the temporal and the spectral components of the light. A global interpretation of the light sensitivity profile of the user may be defined to make the user correspond to a predetermined light sensitivity category, for example from multisensitive to no/slighty sensitive.

Figure 3:
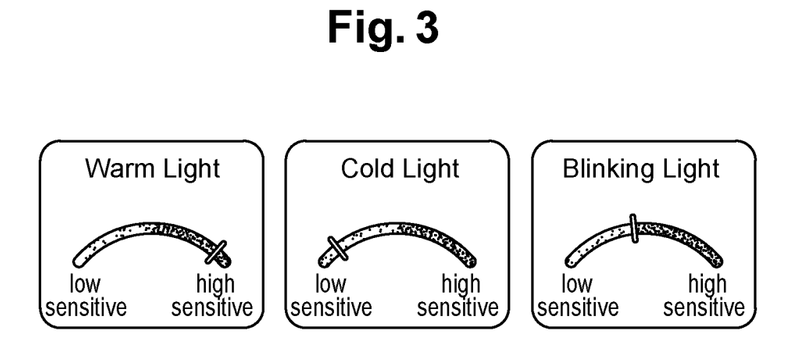
FIG. 3 schematically shows a data restitution regarding the results of the light sensitivity test displayed on displaying device.

As shown on FIG. 3, results obtained during the light sensitivity determining step 100 may be displayed on a displaying device, as a screen of the computer system. Particularly, these results may comprise at least one light sensitivity threshold determined in at least one of said first, second and third measurement steps. Preferably, each light sensitivity threshold is shown compared to a population baseline to allow the user to see its light sensitivity position based on a light sensitivity baseline from the distribution of the global population. Furthermore, the light sensitivity category determined earlier may also be displayed to inform the user regarding the related issues and providing some recommendations.

According to an embodiment, the light sensitivity determining step 100 may comprise a mock step before the first measurement step wherein continuous warm light is emitted toward the user. This mock step allows the user to better understand how the device 10 works and acclimate the user's eyes to the light emission of the device 10.

The user index determining step 200 comprises the determination of a user index representative of the level of protection required by the user, for each light environment among a group of light environments.

By "level of protection required by the user", we mean a level of protection based on answers or inputs coming from the user himself, via a questionnaire. Hence, the purpose of this user index determining step 200 is to determine the user's need protection (anamnesis), which kind of light condition does the user face and for which he needs protection. This index determining step 200 thus allows to determine, and potentially select, the light conditions from which the best filter can be chosen.

The light environments are frequent daily situations that can be a source of discomfort for the user. The group of light environments is selected among a set of environments wherein each environment of the set is associated with a given light level with different light components or characteristic (e.g. intensity, spectral, temporal and spatial components). Particularly, the environments of the set are preferably associated with different combinations of light components or characteristic from each other.

According to a preferred embodiment, each light environment is selected to depict a specific combination of the 4D light components (intensity component, spatial component, spectral component and temporal component). Hence, the group as a whole is determined to have the most representative components of the 4D light components gathered in different light environments. We mean by "light environment" a situation which symbolized by means of a picture and/or words a specific light configuration. For instance, a night situation may imply medium to high light intensity (intensity component) with movable light sources (spatial component) which may be only emitted toward the user during a few seconds (temporal component). The group of light environments preferably comprises at least one outdoor situation, at least one indoor situation and at least one night situation. Each light environment may be symbolized either by an image or by a description representative of the situation.

Figure 4:
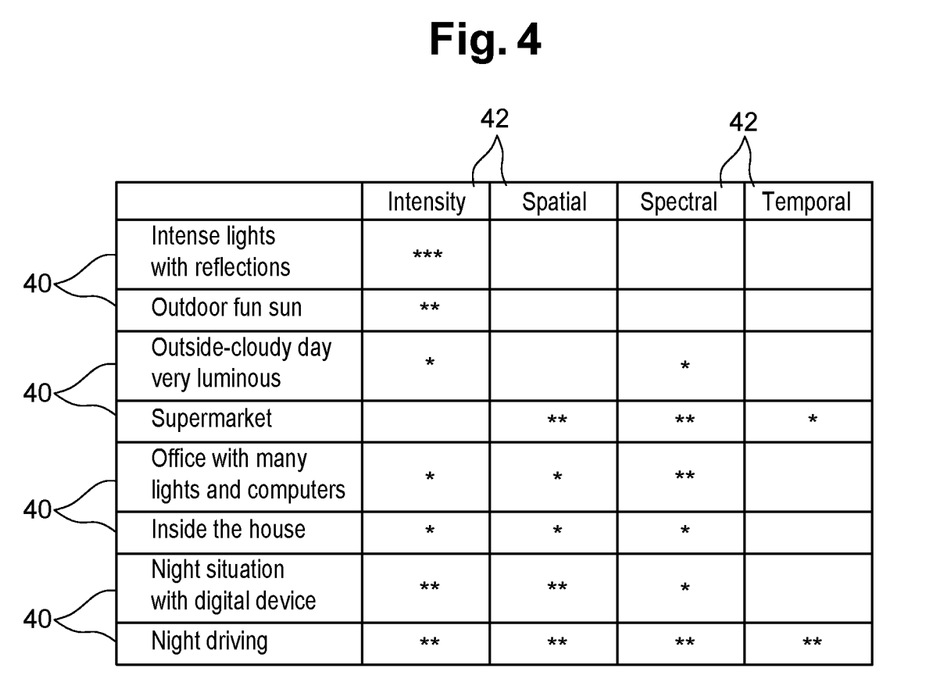
FIG. 4 schematically shows a table listing light environments which can be encountered by a user; light components being defined for each light environment.

According to a preferred embodiment, the group of light environments comprises height light environments 40 which are shown in the table of FIG. 4. Each light environment 40 is defined by a level in each of the 4D light components 42 from a first level (one star) to a third level (three stars). The higher the level is, the more significant the component is. When the component has no evaluation (no star) in a component, this component is meaningless in the light environment. For example, the light environment 40 corresponding to "Night situation with digital device" implies a medium-level of light intensity, a medium-level of spatial component because of the nature of the light source (e.g. a smartphone), a low-level of spectral component and the temporal component is not significant here because the light source is permanent or do not vary over the time.

An image or a description representative of each light environment 40 of the group of environments is provided to the user. In both cases, the image and the description are configured to make the user understand or imagine the light conditions induced by the described light environment 40. The description may be provided to the user either by displaying a text on a displaying device and/or via a soundtrack. For each light environment 40, the user is asked to assess the level of discomfort associated to the light environment 40 and/or the recurrence of this light environment 40. By "recurrence", we mean the frequency at which the user expects to face such a light environment 40.

Figure 5:
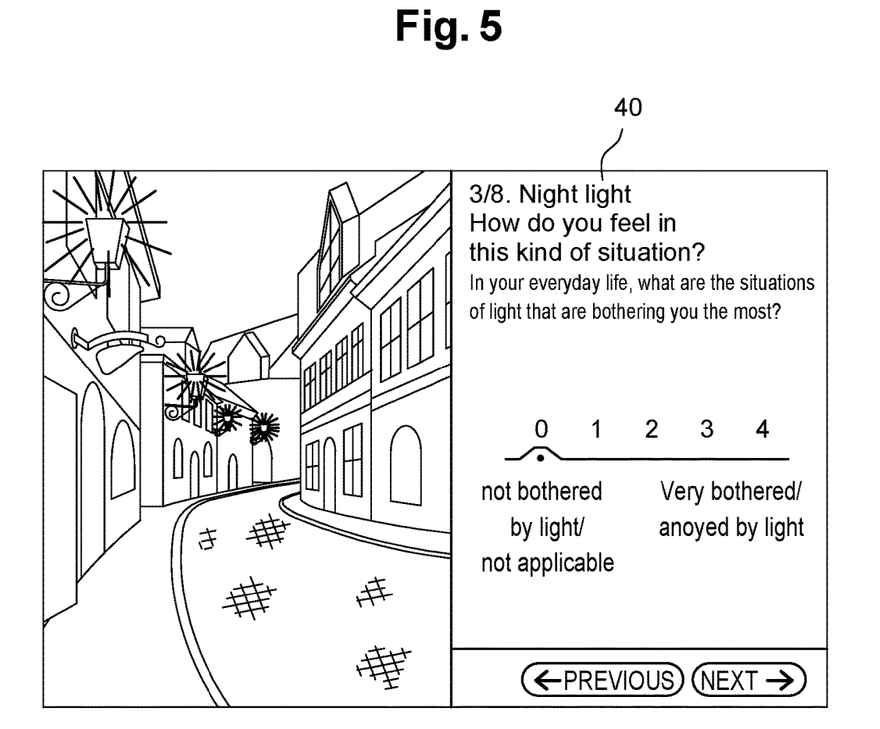
FIG. 5, schematically shows an image of a questionnaire displayed on a displaying device of a computer system wherein the user is asked to assess the level of discomfort and recurrence associated to a given light environment.

According to a preferred embodiment, the light environment 40 is shown as an image representative of this light environment 40 as shown on FIG. 5. The user is asked to assess the level of discomfort and the frequency associated to each light environment 40, for example on a scale from 0 to 4. Preferably, the user interacts with the computer system to provide his answers. The answers of the user are preferably recorded on a memory of the computer system. The images of the light environments 40 are preferably displayed on the displaying device of the computer system.

A discomfort level is then be determined for each light environment 40 of the group depending on the answers of the user.

Figure 6:
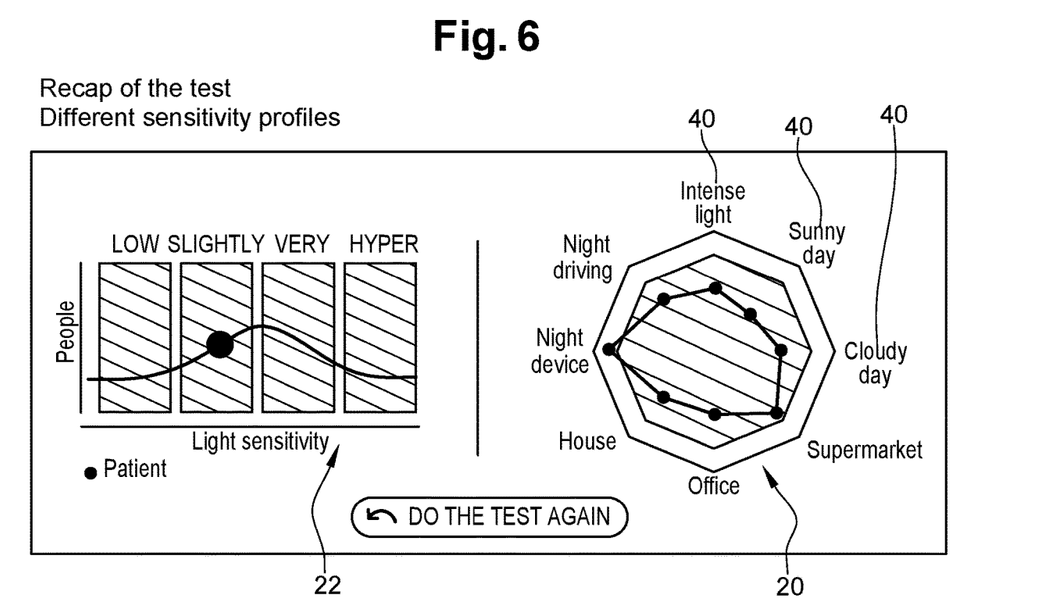
FIG. 6, schematically shows a data restitution regarding the results of the questionnaire displayed on displaying device.

As shown on FIG. 6, the discomfort levels obtained for each light environment 40 may be displayed on the displaying device of the computer system. Particularly, these results may be arranged on a first diagram 20 to allow the user to have a global view of its light sensitivity profile with regard the light environments 40. Furthermore, a second diagram 22 may be displayed showing the light sensitivity of the user compared to a population baseline to allow the user to see its light sensitivity position based on a light sensitivity baseline from the distribution of the global population.

According to a preferred embodiment, light environments 40 having the higher discomfort levels are selected to determine the index representative of the level of protection of the user, called the user index. For instance, if the scale is set from 0 to 4, only the light environments 40 having a discomfort level higher than 2.5 may be selected to determine the user index. The user index is thus determined for each light environment 40 which has been selected.

Figure 7:
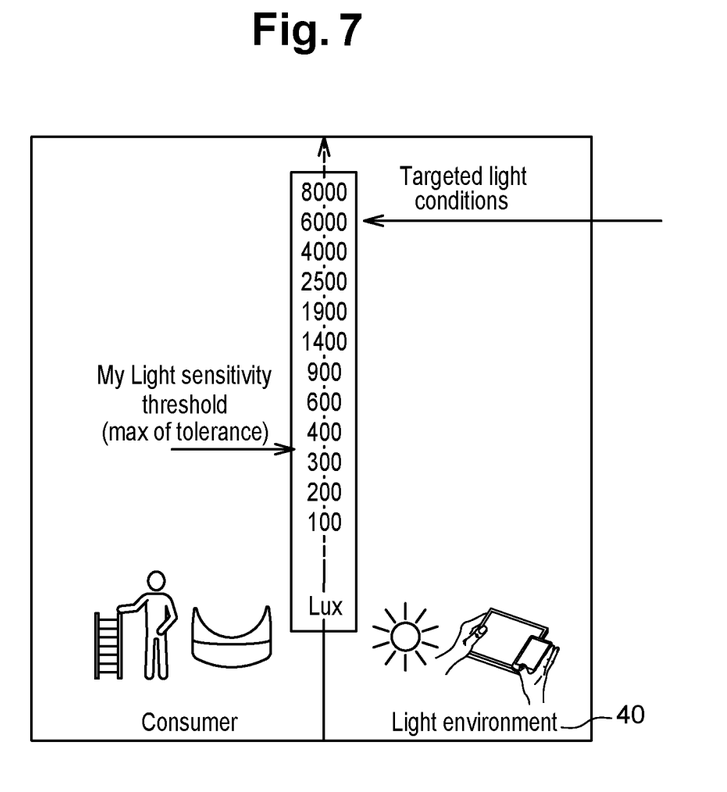
FIG. 7 schematically shows an illuminance scale on which an illuminance of a light environment and a light sensitivity threshold of a user are highlighted.

The user index is determined for a given light environment 40 among the group of light environments 40 by a calculation based on the light level associated with said light environment 40 (intensity component) and on the determined light sensitivity threshold determined in the light sensitivity determining step 100. Particularly, the user index is preferably calculated as the ratio between the light level associated with said light environment 40 and the light sensitivity threshold. For instance, when a light sensitivity threshold of 600 Lux is determined in light sensitivity determining step 100, the user index is equal to 10 for a light environment 40 having a light level of 6000 Lux. It means that the light environment 40 is 10 times more intensive that the consumer can tolerate. As shown on FIG. 7, the user index corresponds to the difference between the light level ("targeted light conditions") of a given environment and the light sensitivity threshold of the user. A user index is then determined for each light environment 40, preferably for each selected light environment 40.

Then, a score for each light environment 40 and for a plurality of filters is determined at the score determining step 300. As shown on FIG. 8, the score determining step 300 comprises a step 310 for determining an index representative of the protection provided by a given filter, called the filter index. Each filter of the plurality of filter is at least defined by a filtering ability. According to a preferred embodiment, the filtering ability comprises a luminous transmittance value (Tv) of the given filter. The luminous transmittance (Tv) is a ratio of the luminous flux transmitted by the lens or filter to the incident luminous flux. The luminous transmittance defines the percentage of light from a light flux transmitted through the filter. Hence, a surface with a luminous transmittance of 0% prevents the whole light flux to pass through the surface whereas a surface with a luminous transmittance of 100% allows the whole light flux to pass through it without absorbing it.

The luminous transmittance in the visible spectrum may be determined using the equation as follows:

$$Tv = 100 \times \frac{\int_{380\,nm}^{780\,nm} T(\lambda) \cdot V(\lambda) \cdot S_{D65\lambda}(\lambda) \cdot d\lambda}{\int_{380\,nm}^{780\,nm} V(\lambda) \cdot S_{D65\lambda}(\lambda) \cdot d\lambda} \%$$

where $T(\lambda)$ is the spectral transmittance of the tinted spectacle lens;

$V(\lambda)$ is the spectral luminous efficiency function for daylight (see ISO/CIE 10527);

$S_{D65\lambda}(\lambda)$ is the spectral distribution of radiation of the illuminant D 65 according to the standard of the International Commission on illumination (see ISO/CIE 10526).

Figure 8:
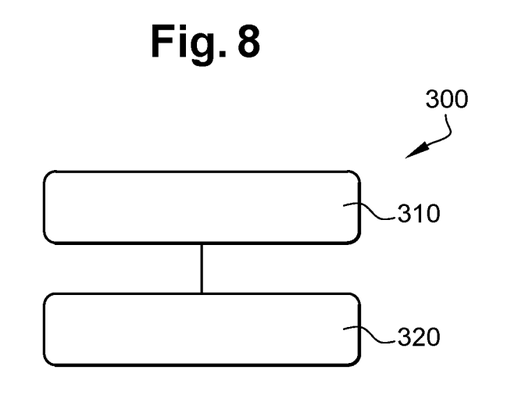
FIG. 8 shows a flowchart of a score determining step.

The filter index determining step 310 first comprises a step of determining the filtering ability of each filter of the plurality of filter. Then, the filter index of each filter is determined using the equation as follows:

$$\text{Filter index} = \frac{100}{Tv}$$

The filter index thus defines the amount of light cut by the filter. A filter may have a single luminous transmittance value, i.e. a fixed value, or a plurality of luminous transmittance values, as a photochromic or electrochromic lens. In the case where the filter is a varying filter, the lower and higher luminous transmittance values are preferably calculated to determine the compliance of the filter to the user for each lower and higher luminous transmittance values.

Figure 9:
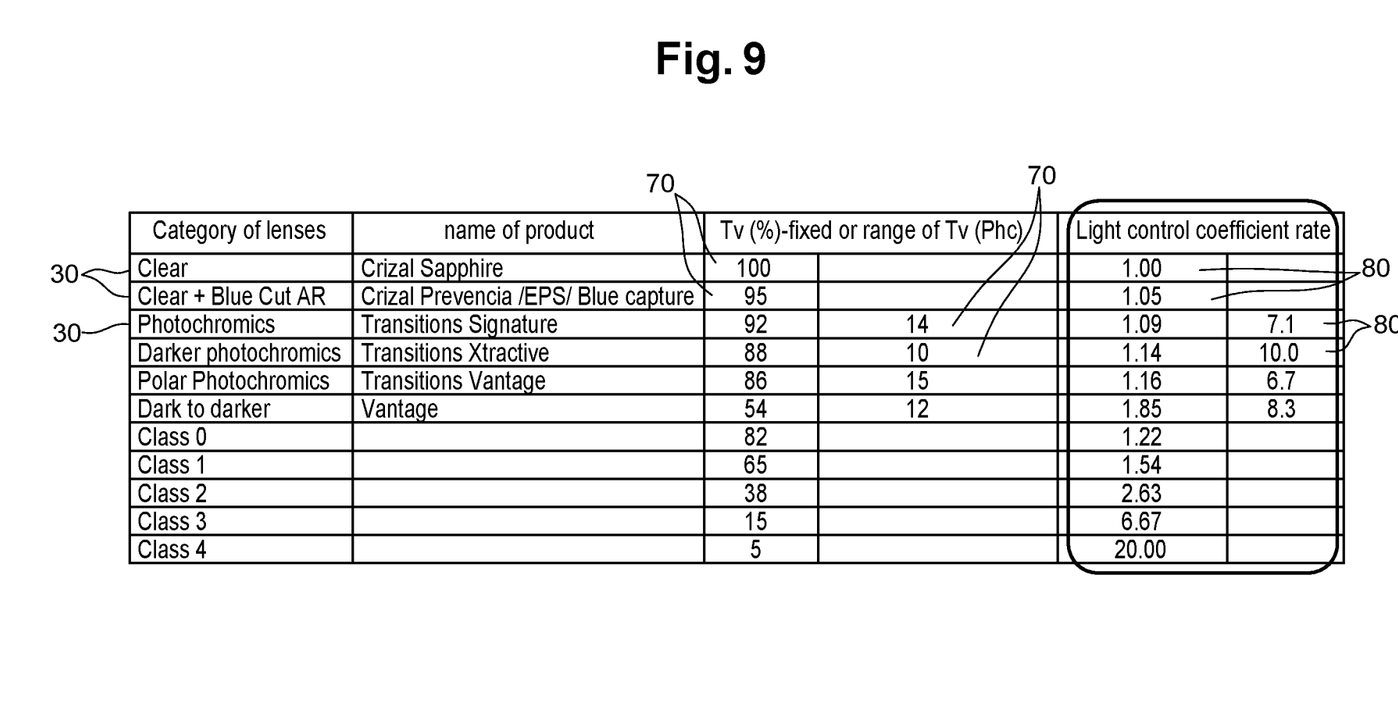
FIG. 9 shows schematically a table gathering filter references and associated luminous transmittance and filter index.

FIG. 9 shows an example of a table gathering a plurality of filter references 30 having each one or more luminous transmittance values 70 and for which a filter index 80 is determined using the equation above. The filters shown in the table have a luminous transmittance from 5% to 100%.

The score determining step 300 further comprises a score calculation step 320 for determining the score for each light environment 40 among the group of light environments 40 and for each filter among a group of filters. Said score is representative of the effectiveness of a filter in a given situation, i.e. the ability of a given filter to reach the level of protection required by the user. The score for a given filter and a given light environment 40 is calculated based on the user index in said given light environment 40 and the filter index of said given filter. Particularly, the score is calculated as the ratio between the user index and the filter for said given filter and said given light environment 40. For instance, the score is equal to 1 for a filter index of 6.67 and a user index of 6.67. A score of 1 means that the filter covers 100% of the user's protection needs for said light environment 40. If a filter index is higher than 1, it means that the filter fully protects the user so that light comfort is optimal but there is a risk of vision loss.

The score is therefore a score representative of the compliance for a user of a given filter in a given light environment 40. Providing the score for selected light environment 40 which have been identified by the user as having a high level of discomfort and/or recurrence allows to help determining the best protection for the user.

Figure 10:
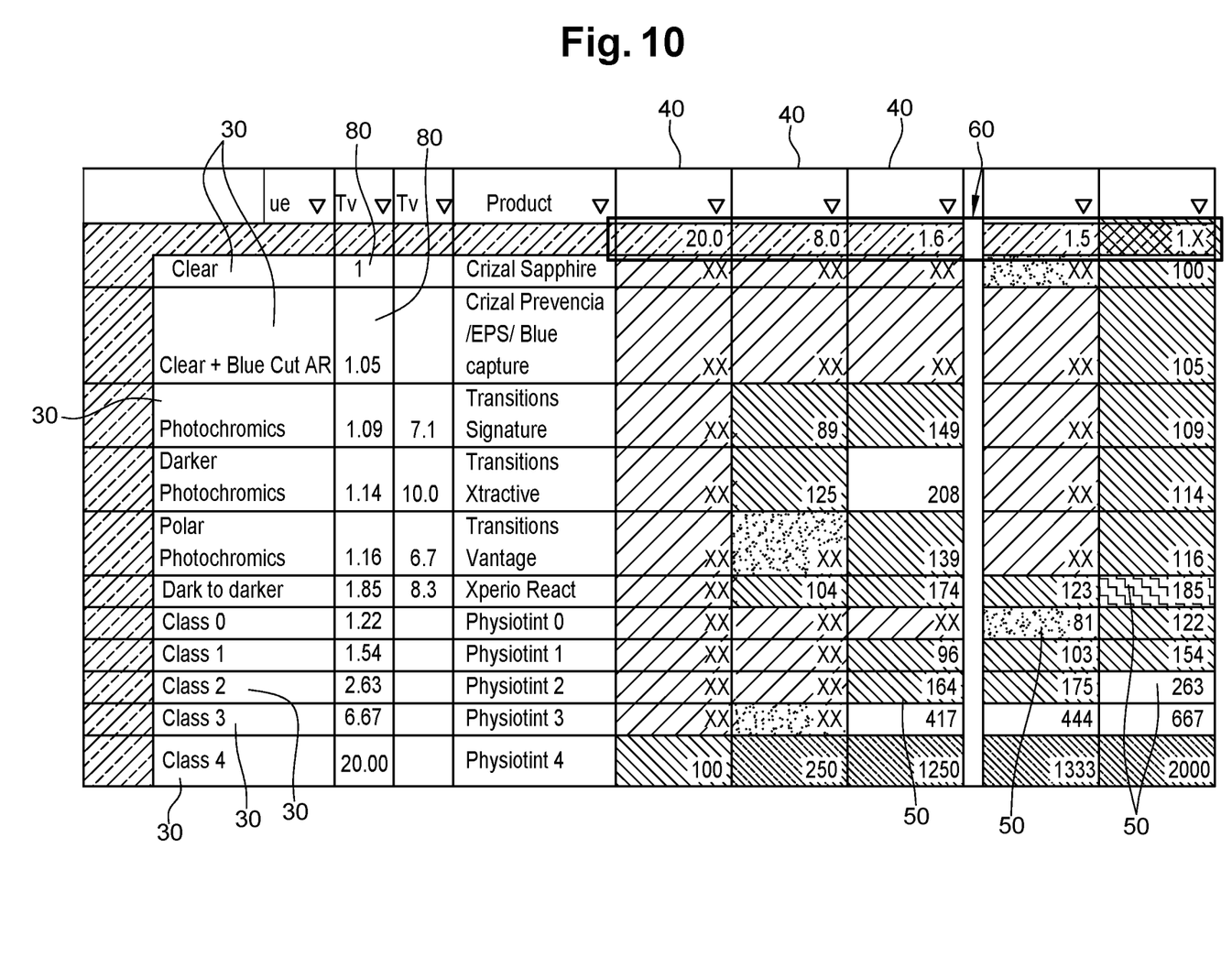
FIG. 10 shows schematically a table gathering filter references and associated scores for each selected light environment.

FIG. 10 shows an example of a table gathering a plurality of scores 50 determining base on a plurality of filter references 30 for which a filter index has been determined in filter index determining step 310 and a plurality of selected light environments 40 for which user indexes 60 has been determined in user index determining step 200. For instance, it can be seen that the score is equal to 5% (or 0.05) for a user index of 20 for a filter index of 1. As another example, it can be seen that the score is equal to 96% (or 0.96) for a user index of 1.6 for a filter index of 1.54.

Then, the filter determining step 400 comprises the determination of at least one filter based on the scores 50 determined at the score determining step 300. This filter determining step 400 aims at ranking the filters 30 based on their scores 50 for the light environments 40. Preferably, the filters 30 are ranked only with regard to the light environments selected by the user.

Each score 50 is associated with a value representative of the compliance of a given filter 30 in a given light environment 40 in view of the level of protection required by the user. Then, a global value may be determined based on all the values determined for a same filter. All the values of a same filter for each light environment 40 or each selected light environment 40 may be added to obtain this global value. The plurality of filters 30 are then ranked based on the global values.

According to a preferred embodiment, one or more filters are determined for at least two transparent supports having different purposes. For example, when the transparent support is an ophthalmic lens, one or more filters are determined for at least two spectacles having different use. One spectacle may be used as sunglasses and another spectacle may be used as everyday eyeglasses. The ranking of the filters is performed with regard to specific light environment which are associated to the use of the transparent support.

According to a preferred embodiment, the closer to 100% the score is, the higher the value is. Particularly, scores from a low compliance threshold to a high compliance threshold may be associated to a positive value whereas scores out of this compliance range may be associated to a negative value. In doing so, the global value of each filter is weighted based on a predetermined degree of compliance to the user's need. For instance, the compliance range may be set from 86% to 200%. Furthermore, scores 50 which are considered to be significantly non-compliant to the user's need, e.g. scores under 50% and above 300%, may be associated to a low value. As an example, scores between 86% and 200% are associated with a value of 2, scores lower than 50% or high than 300% are associated with a value of −2 and scores from 51% to 85% or from 201% to 299% are associated with a value of −0.5. Therefore, if we consider a filter having scores equal to 42, 104, 174, 123 and 185, the respective associated values would be −2, 2, 2, 2 and 2. The global value, i.e. the sum of the values, would be 6. The scores which are summed are at least those which have been selected in the index determining step 200.

One or more filters may be then determined to have the best compliance with the user's protection need. Preferably, at least two filters from different categories of filters are determined to provide the user or the ECP with a broader list of compliant filters. Preferably, these different filter categories correspond to different purposes or for different pair of spectacles. Different categories of filter may be filters intended to be put on sunglasses and filters intended to be put on everyday eyeglasses.

Figure 11:
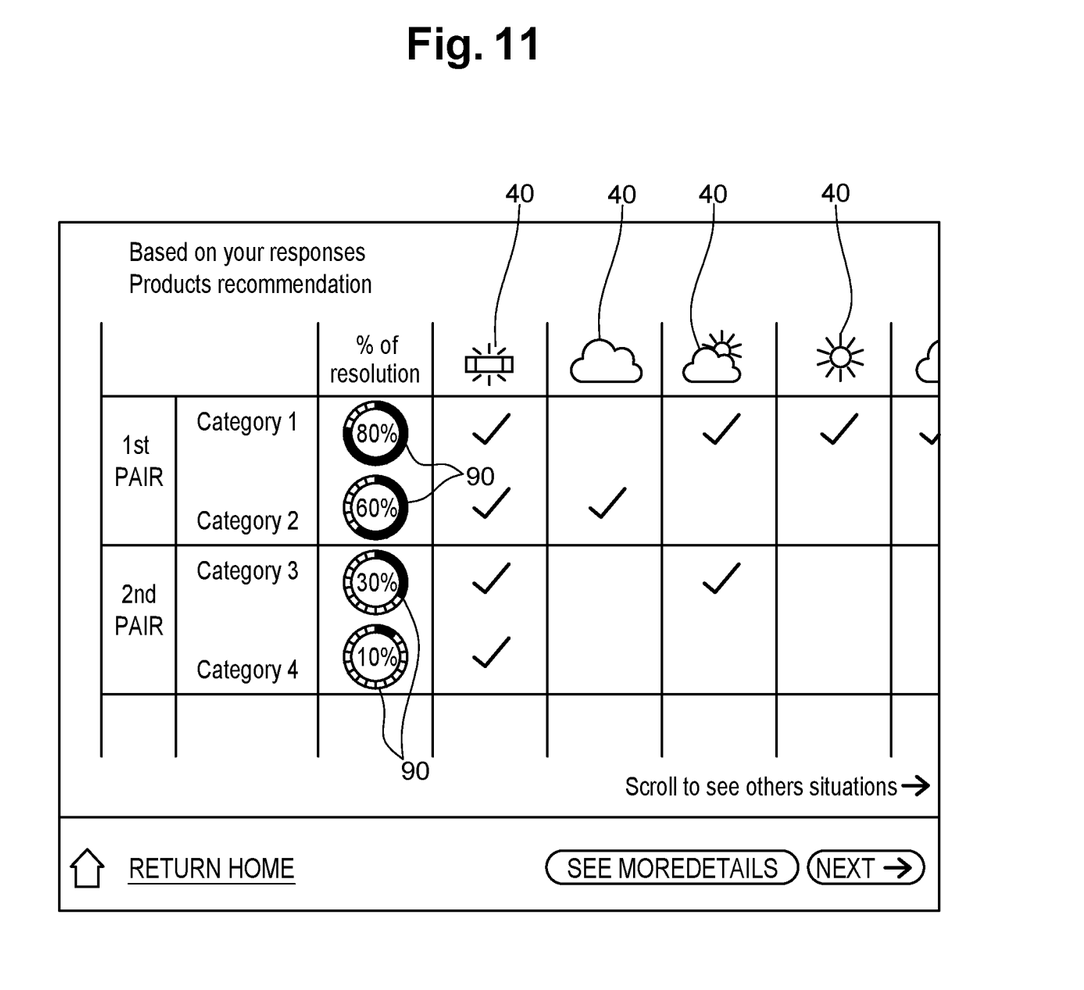
FIG. 11 shows schematically a data restitution of a filter determining step displayed on displaying device.

As shown on FIG. 11, the one or more filters which have been determined as the most compliant with the user's protection needs may be displayed on the displaying device of the computer system. Particularly, an information representative of the compliance of each filter with regard to each light environment 40 or selected light environment 40 may be displayed. A percentage of resolution 90 of each filter may be also determined and optionally displayed based on the median of the percentage of efficiency for all the selected light environments 40 to give a global performance of each filter.

As mentioned above, the filter determining method may be a computer-implemented method which can be performed using code instructions from a computer program product or a computer system. The computer system comprises a processor; and a memory with computer code instructions stored thereon. The memory operatively is coupled to the processor such that, when executed by the processor, the computer code instructions cause the computer system to perform the filter determining method.

The invention claimed is:

1. A method for determining at least one filter for a transparent support able to improve or to maintain the visual comfort and/or visual performance of a user, the method comprising:
   determining a quantity representative of a light sensitivity threshold of the user, wherein said quantity representative of a light sensitivity threshold is an objective parameter or a parameter obtained using a measurement/calculation process;
   determining, for each light environment among a group of light environments, an index representative of the level of protection required by the user;
   determining a score for each light environment among the group of light environments and for each filter among a group of filters, said score being representative of the capacity of the filter to reach the level of protection required by the user;
   determining at least one filter among the group of filters based on the scores of said at least one filter in a plurality of light environments among the group of light environments.

2. The method according to claim 1, wherein the group of light environments is selected among a set of environments; each environment of the set of environments being associated with a given light level.

3. The method according to claim 1, wherein the environments of the set of environments are associated with light levels different from each other.

4. The method according to claim 2, wherein the group of light environments is selected among the set of light environments based on a questionnaire assessing the recurrence of each light environment for the user and/or the level of discomfort of each light environment for the user.

5. The method according to claim 1, wherein the index representative of the level of protection required by the user in a given light environment among the group of light environments is calculated based on the light level associated with said light environment and on the determined light sensitivity threshold.

6. The method according to claim 1, wherein the score for a given filter and a given light environment is calculated based on the index representative of the level of protection required by the user in said light environment and an index representative of the protection provided by said filter.

7. The method according to claim 6, wherein the index representative of the protection provided by a given filter is determined based on the luminous transmittance (Tv) of the given filter.

8. The method according to claim 1, wherein the light sensitivity threshold is determined using a device configured to expose the user to an increasing light level and to determine the user's light sensitivity threshold based on a user's feedback representative of a discomfort.

9. The method according to claim 8, wherein the light sensitivity threshold is determined when the user is exposed to at least one light condition among a warm light, a cold light and a blinking light.

10. The method according to claim 1, wherein the step of determining at least one filter comprises:
    associating each score with a value representative of the compliance of a given filter in a given light environment in view of the level of protection required by the user;
    for a plurality of filters among the group of filters, calculating the sum of the values of the plurality of light environments; and
    ranking the plurality of filters using the sum obtained at preceding step.

11. The method according to claim 1, further comprising at least one of the following steps:
    displaying on a displaying device the light sensitivity threshold using a predetermined scale based on a population baseline;
    displaying on the displaying device a discomfort level representative of the level of discomfort declared by the user for each light environment among the group of light environments; or
    displaying on the displaying device the at least one filter determined among the group of filters.

12. The method according to claim 1, wherein the method is a computer-implemented method.

13. A computer system for determining at least one filter for a transparent support able to improve or to maintain the visual comfort and/or visual performance of a user, the system comprising:
    a processor; and
    a memory with computer code instructions stored thereon, the memory operatively coupled to the processor such that, when executed by the processor, the computer code instructions cause the computer system to perform a method for determining at least one filter for a transparent support able to improve or to maintain the visual comfort and/or visual performance of a user, the method comprising:
        determining a quantity representative of a light sensitivity threshold of the user wherein said quantity representative of a light sensitivity threshold is an objective parameter or a parameter obtained using a measurement/calculation process;
        determining, for each light environment among a group of light environments, an index representative of the level of protection required by the user;
        determining a score for each light environment among the group of light environments and for each filter among a group of filters, said score being representative of the capacity of the filter to reach the level of protection required by the user;

determining at least one filter among the group of filters based on the scores-of said at least one filter in a plurality of light environments among the group of light environments.

\* \* \* \* \*